United States Patent
Regensburger et al.

(10) Patent No.: US 12,053,329 B2
(45) Date of Patent: Aug. 6, 2024

(54) ULTRASOUND-BASED CHARACTERIZATION OF PARTICLES IN A FLUID-FILLED HOLLOW STRUCTURE

(71) Applicant: Siemens Healthcare GmbH, Erlangen (DE)

(72) Inventors: Alois Regensburger, Poxdorf (DE); Jens-Christoph Georgi, Oberasbach (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 17/717,433

(22) Filed: Apr. 11, 2022

(65) Prior Publication Data
US 2022/0338844 A1    Oct. 27, 2022

(30) Foreign Application Priority Data
Apr. 22, 2021   (DE) .................... 10 2021 204 041.1

(51) Int. Cl.
*A61B 8/00*   (2006.01)
*A61B 8/08*   (2006.01)

(52) U.S. Cl.
CPC ............. *A61B 8/54* (2013.01); *A61B 8/0891* (2013.01); *A61B 8/58* (2013.01); *A61B 2560/0223* (2013.01)

(58) Field of Classification Search
None
See application file for complete search history.

(56) References Cited

U.S. PATENT DOCUMENTS

2007/0238953 A1 * 10/2007 Lucassen ............... G01N 29/06
                                                      600/407
2008/0139942 A1    6/2008 Gaud et al.
(Continued)

FOREIGN PATENT DOCUMENTS

DE   102010031129 A1   1/2012
EP      3637098 A1 *   4/2020   ............... G01F 1/66
(Continued)

OTHER PUBLICATIONS

Pekar et al. ("Quantitative imaging performance of frequency-tunable capacitive micromachined ultrasonic transducer array designed for intracardiac application", Ultrasonics, 84, (2018) 421-429) (Year: 2018).*

(Continued)

*Primary Examiner* — Patrick Fernandes
*Assistant Examiner* — Marjan Saboktakin
(74) *Attorney, Agent, or Firm* — Lempia Summerfield Katz LLC

(57) ABSTRACT

In accordance with a method for characterization of particles in a fluid-filled hollow structure, an ultrasound signal with a frequency spectrum, which exhibits a local maximum at a variable measurement frequency, is emitted in the direction of a part area of the hollow structure and reflected components are detected. The measurement frequency is tuned in a predetermined measurement interval, and depending on the detected reflected components, a spectral response curve is acquired as a function of the measurement frequency. Depending on the response curve, at least one characteristic property for a part of the particles located in the part area of the hollow structure is determined. The characteristic property includes a measure for an adhesion of the particles of the part of the particles located in the part area of the hollow structure.

22 Claims, 1 Drawing Sheet

(56) References Cited

U.S. PATENT DOCUMENTS

2009/0117033 A1* 5/2009 O'Gara ............... A61K 9/0024
                                                                                                    424/501
2013/0104657 A1   5/2013 Lin et al.
2013/0260396 A1* 10/2013 Akcakir ............... G03H 1/0443
                                                                                                    435/7.25

FOREIGN PATENT DOCUMENTS

EP           3637098 A1     4/2020
WO        2006094951 A1     9/2006
WO    WO-2006094951 A1 * 9/2006  ........... A61K 49/223

OTHER PUBLICATIONS

Truong et al. ("Resonant Rayleigh light scattering of single Au nanoparticles with different sizes and shapes", Nanoscale 2014, 6, 2307-2315) hereinafter "Truong". (Year: 2014).*

Pekar, Martin et al., "Quantitative imaging performance of frequency-tunable capacitive micromachined ultrasonic transducer array designed for intracardiac application: Phantom study," Ultrasonics, vol. 84, pp. 421-429, (2018).

* cited by examiner

ULTRASOUND-BASED CHARACTERIZATION OF PARTICLES IN A FLUID-FILLED HOLLOW STRUCTURE

The present patent document claims the benefit of German Patent Application No. 10 2021 204 041.1, filed Apr. 22, 2021, which is hereby incorporated by reference in its entirety.

TECHNICAL FIELD

The present disclosure relates to a method for characterization of particles in a fluid-filled hollow structure and to a corresponding ultrasound system as well as to a computer program product.

BACKGROUND

Within the framework of the method that is known as tumor embolization, particles, in particular small beads, in the micrometer range are introduced via a catheter into a blood vessel supplying a tumor. On the one hand, these particles may throttle the flow of blood through the vessel and thus the supply to the tumor. On the other hand, the particles may have chemotherapeutics added to them, for example, which they may administer to the tumor tissue. The introduction of radioactive particles into the vicinity of the tumor is also possible in a similar way.

In order to be able to estimate or monitor the success or the status of the tumor embolization, it is desirable to determine the local concentration of the particles or the proportion of particles adhering to vessel walls or other objects or other characteristic properties of the introduced particles.

A throughflow measurement arrangement with an ultrasound sensor for carrying out a measurement method for measuring the particle size distribution and particle concentration in lines through which liquid is flowing is known from publication EP 3 637 098 A1.

An ultrasound particle measurement system with an ultrasound transducer, which has an ultrasound transducer element and a coupling element, is known from publication DE 10 2010 031 129 A1. Acoustic signals are able to be transmitted and received from the ultrasound transducer element via the coupling element. The coupling element is embodied as an acoustic lens. With an evaluation unit suitable for amplitude analysis of reflection signals of the acoustic signals reflected from particles to the ultrasound transducer, it is possible to count a number of amplitudes of the reflection signals in a predetermined time interval that is greater than a predetermined threshold value.

A medical imaging system for providing echo signals, which show a reaction of a part of the body to a plurality of pulsed ultrasound waves with different sound pressures, is known from publication WO 2006/094951 A1. In this case, the part of the body includes tissue through which a contrast medium is flowing. Means are further included for distinguishing a contribution of a first contrast medium type from a contribution of a second contrast medium type and of the tissue in the echo signals.

The publication entitled PEKAR, Martin et al., "Quantitative imaging performance of frequency-tunable capacitive micromachined ultrasonic transducer array designed for intracardiac application: Phantom study," Ultrasonics, Volume 84, 2018, pp. 421-429, investigates the extent to which, through frequency tuning of an ultrasound system, both images with enhanced local resolution and also images with a greater penetration depth may be created.

SUMMARY AND DESCRIPTION

An object of the present disclosure is to make possible an option for characterization of particles in a fluid-filled hollow structure, in particular in a blood vessel.

The scope of the present disclosure is defined solely by the appended claims and is not affected to any degree by the statements within this summary. The present embodiments may obviate one or more of the drawbacks or limitations in the related art.

The disclosure is based on creating an ultrasound signal with variable measurement frequency and evaluating the signal according to reflected components in order to acquire a spectral response curve, with the aid of which at least one characteristic property of the particles in the hollow structure is determined.

In accordance with one aspect, a method for characterization of particles in a fluid-filled hollow structure is specified. In the method, in particular, by an ultrasound probe actuated by a control unit, an ultrasound signal with a frequency spectrum that exhibits a local maximum at a variable measurement frequency is emitted in the direction of a part area of the hollow structure and reflected components of the ultrasound signal are detected, in particular, by the ultrasound probe. The measurement frequency is tuned, in particular by the control unit, in a predetermined measurement interval, and depending on the detected reflected components, a spectral response curve is acquired as a function of the measurement frequency. Depending on the response curve, at least one characteristic property for at least one part of the particles that is located in the part area of the hollow structure is determined, in particular by an evaluation unit. The one characteristic property includes a measure of which component of the particles in the part area is adhering to the hollow structure itself, in particular to its inner walls, or to other objects such as catheters, other instruments or other tissue and what proportion of the particles is moving freely through the fluid.

The hollow structure may involve a tubular or branched tubular structure with solid of flexible walls, through which the ultrasound signal may pass at least in part in order to reach the particles. In particular, the hollow structure involves a human or animal vessel structure or a human or animal blood vessel.

The fluid with which the hollow structure is filled with a gas or a liquid. In certain embodiments, the fluid is a liquid. In the case of a blood vessel as hollow structure, the fluid is a liquid that contains blood. The liquid may moreover include other liquids, for example, to support the introduction of the particles, such as a cooking salt solution, a contrast medium, or the like.

The method starts in this case from a situation in which the particles are present in the fluid-filled hollow structure, in particular are introduced beforehand, in the case of a blood vessel for example by a corresponding catheter. The act of introducing the particles however, in the case of a human or animal vessel as the hollow structure, is not part of the method. Also, the introduction where necessary of the catheter and measures necessary for this are not part of the method.

Depending on the form of embodiment of the ultrasound system used for the method, the ultrasound probe may be configured to emit the ultrasound signal from outside the object including the hollow structure, (e.g., from outside the human or animal body), in the direction of the part area of the hollow structure. As an alternative, the ultrasound probe may also be configured for insertion into the hollow structure or into a further hollow structure arranged in the environment of the hollow structure, (e.g., for endocorporeal use). For example, the ultrasound probe may be configured for endocavitary, endoscopic, and/or endovascular use. In the case of human or animal vessels or blood vessels as the hollow structure, the introduction of the ultrasound probe into the human or animal body is not part of the method. In particular, a movement to change the position of the ultrasound probe within the human or animal body is not part of the method. It should be pointed out, however, that the acts of the method may also be carried out repeatedly and the position of the ultrasound probe may be changed between the individual repetitions.

The measurement frequency being able to be varied may be understood in such a way as the measurement frequency, e.g., the maximum point of the frequency spectrum of the ultrasound signal, which may also be referred to as the central frequency, being able to be adjusted, in particular by the control unit. When the measurement frequency has been adjusted then the frequency does not change until such time as it is adjusted again to another value by the control unit.

The tuning of the measurement frequency may therefore be understood as a controlled discrete or quasi-continuous variation or adjustment of the measurement frequency within the measurement interval, so that at least two, (e.g., a plurality), or within the framework of the frequency resolution that may be achieved, all frequencies, are adjusted in the measurement interval.

The reflected components of the ultrasound signal, which may be detected by the measurement probe, may be assigned to the measurement frequency of the ultrasound signal emitted. Based on the reflected component in each case, the ultrasound probe creates a measurement signal that corresponds to the strength or amplitude of the reflected components at an evaluated frequency. The evaluated frequency may be equal to the measurement frequency or for example equal to a multiple of the measurement frequency, e.g., may correspond to a higher harmonic of the measurement signal.

An amplitude of the measurement signal may correspond to the value of the response curve at the corresponding measurement frequency. The response curve may be a location-dependent response curve. In particular, a separate response curve may be acquired in the way described for different part areas of the hollow structure. In this way, the characteristic property for various components of the particles that are located in the corresponding various part areas of the hollow structure may be determined.

The particles in particular involve particles with a spatial extent in the micrometer range through to hundreds of micrometers. The extent of the particles may be understood as the maximum extent of the particles. For example, the geometric form of the particles is approximately spherical, so that the extent of a particle involves its diameter. The particles may have an extent in the range of 10 μm to 500 μm, or in the range of 50 μm to 300 μm.

The extent of the particles may follow a corresponding distribution with a maximum in one of the value intervals. The width of the distribution, (e.g., the standard deviation of the distribution), may lie in the range of 1 to 10 percent of the maximum of the distribution, or in the range of 2 to 5 percent of the maximum of the distribution. For example, the width of the distribution or the standard deviation may lie in the range of 1 μm to 10 μm, or in the range of 4 μm to 6 μm, for example, at about 5 μm.

Depending on the manufacturing method of the particles, which includes a plastic material or may include a plastic material, (e.g., a polyvinyl alcohol), the size distribution of the particles may correspond to the specification in advance. If this is not the case, the particles may be filtered, sorted, centrifuged, or treated in a similar way depending on their extent, so that particles with correspondingly suitable size distributions may be selected.

The particles, which are also referred to inter alia as embolization beads, may involve particles that only act mechanically, e.g., may impede the fluid in the hollow structure as it flows through the hollow structure. In certain examples, the beads may also have a medicament, (e.g., a chemotherapeuticum), added to them. In this context, the beads are thus also referred to as drug-eluting beads. Moreover, radioactive materials may be used as particles where necessary or the particles may have radioactive materials added to them.

In accordance with the disclosure, the spectral dependency of the ultrasound reflection on small particles may also be utilized to deduce their characteristic properties. The at least one characteristic property may include a number of particles in the part area or a concentration of particles in the fluid in the part area or another measure for the amount of the particles in the part area of the hollow structure.

On the one hand, the intensity or strength of the reflected proportions is a measure of how many particles reflect and return the emitted ultrasound signal in the part area, so that the measure for the amount of the particles may be deduced. An adhesion of the particles restricts the movement or specific movement modes of the particles or modifies these movement modes. Through this, the form of the response curve is dependent on the proportion of the adhering particles or on the proportion of the freely moving particles in the hollow structure. Through a corresponding evaluation, the measure for the adhesion of the particles may thus be deduced.

Because the characteristic properties of the particles, (e.g., their local concentration and their degree of adhesion for their part), are of great relevance for the intended function of the particles, (e.g., the throttling of the fluid flow or the release of medicaments, such as for estimating the progress and the success of the corresponding measure), a corresponding observation may be supported by the disclosure.

For example, a result of the method, such as the at least one characteristic property, may also be displayed on a display unit for different part areas of the hollow structure, encoded according to brightness and/or color. This display may also be shown overlaid with a conventional ultrasound image, so that the user is provided with an especially informative and quick-to-grasp presentation of the characteristic properties.

In accordance with at least one form of embodiment of the method, in particular by the evaluation unit, a first measure for an amount of the particles of the part of the particles that are located in the part area of the hollow structure is determined.

In other words, the at least one characteristic property includes the first measure. The first measure may involve a number or a relative number of the particles in the part area or a concentration of the particles in the part area.

In accordance with at least one form of embodiment, in particular by the evaluation unit, an amplitude value of the response curve is determined at a predefined frequency value of the measurement frequency in the measurement interval. The first measure is determined depending on the amplitude value.

The frequency value may be predefined by being predetermined as a constant numerical value or by the frequency value being determined in a predefined way from the response curve. For example, the frequency value may correspond to a local or global maximum point of the response curve, a minimum value of the measurement interval, a maximum value of the measurement interval, or an average value of the measurement interval, and so forth.

The first measure may be directly proportional or equal to the amplitude value or may be calculated depending on the amplitude value. For example, the first measure may correspond to the ratio of the amplitude value to a further amplitude value of the response curve at another measurement frequency, for example, a maximum amplitude difference of the response curve and so forth. The first measure may also correspond to a ratio of the amplitude value to a predetermined reference value.

In accordance with at least one form of embodiment, the frequency value corresponds to a local maximum point of the response curve, the amplitude value thus corresponds to a local maximum of the response curve.

In other words, the frequency value involves a resonant frequency or a mid-resonant frequency of the particles.

In accordance with disclosure, it is not necessary, during tuning of the measurement frequency, for the resonant frequency of the particles to be met or exceeded. Also, the course of the response curve outside the resonance range may be included for characterization. The analysis of the range around the resonant frequency however thus enables there to be an especially reliable evaluation.

In accordance with at least one form of embodiment, in particular by the evaluation unit, depending on the response curve, a second measure for an adhesion of the particles of the part of the particles that is located in the part area of the hollow structure is determined. In other words, the at least one characteristic property includes the second measure.

The adhesion may be understood as the restriction of the free movement of the particles in the fluid. The particles may adhere to the hollow structure itself, in particular to an inner wall of the hollow structure, to an instrument in the hollow structure, such as a catheter or guide wire, to another part of the tissue, or to other particles.

The second measure may likewise involve a number, a relative number or a concentration of adhering particles. As an alternative, it may also involve a number, a relative number or a concentration of particles that adhere, e.g., which may move freely in the fluid.

In accordance with at least one form of embodiment, at least one curve property of the response curve is compared, in particular by the evaluation unit, with a predetermined reference curve property, in particular a predetermined reference curve. The second measure is determined depending on a result of the comparison.

The reference curve may involve a frequency response idealized or previously determined, (e.g., determined in vitro), in the measurement interval for particles correspondingly freely movable in the fluid. Through the comparison it is thus quantified how greatly the response curve deviates in the at least one curve property from the reference curve, thus how greatly the properties of the particles in the part area of the hollow structure differ from freely moving particles.

The at least one curve property in such cases may include a width of a resonance peak, a central frequency of the resonance peak, in particular a position of the maximum point, a rise in a specific area of the curve and so forth. The at least one curve property may be determined for example via a curve fit. In other words, a curve of a specific shape may be fitted to the response curve and the at least one curve property may be derived from the resulting fit.

In this way, the second measure for the adhesion of the particles may be deduced via the curve properties. Through the adhesion, the resonance peak tends to widen out or the maximum point tends to shift. The wider the corresponding peak is compared to the reference curve or the more greatly shifted is the maximum point compared to the reference curve in the response curve, the greater is the number of adhering particles.

In accordance with at least one form of embodiment, a characteristic correlation value based on the response curve and a predetermined reference curve is determined, in particular by the evaluation unit. The second measure is determined depending on the characteristic correlation value.

The characteristic correlation value may correspond in this case to a value of a convolution integral of the response curve with the reference curve. For example, the characteristic correlation value K may be given by:

$$K \sim \int A(f)R(f-x)df|_{x=0} = \int A(f)R(f)df,$$

wherein A(f) represents the response curve and R(f) the reference curve as a function of the measurement frequency f.

In accordance with at least one form of embodiment, the measurement interval lies within a range of 5 MHz to 12 MHz. In other words, the measurement interval is a part interval of the interval of 5 MHz to 12 MHz.

This range may be referred to as the high-frequency ultrasound range. The higher the frequency of the ultrasound signal is, the higher is the spatial resolution that may be achieved, the lower however is the range of the ultrasound signal. It has been shown that in the interval a suitable compromise between range and resolution may be obtained.

In accordance with at least one form of embodiment, a bandwidth of the frequency spectrum of the emitted ultrasound signal is greater than or equal to 1 kHz and less than or equal to 100 kHz.

The bandwidth corresponds to a contiguous area in the frequency spectrum, within which the amplitude of the individual frequency components of the ultrasound signal is greater than or equal to a predetermined threshold value. In one example, the amplitude of the ultrasound signal in the frequency space outside the area defining the bandwidth is equal to zero and within the area is not equal to zero.

The smaller the bandwidth is, the longer are the corresponding pulses of the ultrasound signal in the time domain. Through this, the axial resolution of the ultrasound measurement also falls, e.g., the resolution in the propagation direction of the ultrasound signal, with falling bandwidth, the more narrowband the measurement is. The more narrowband the measurement is, however, the higher is the resolution in the frequency domain with which the response curve may be created, e.g., a resonance may be resolved if necessary. The range for the bandwidth represents a suitable compromise.

In certain examples, the narrowband measurement may also be supplemented by recordings with a higher bandwidth, in order to obtain a correspondingly higher axial resolution and transmit the creation and ultrasound signal with the smaller bandwidth adapted accordingly.

In accordance with at least one form of embodiment, before the emission of the ultrasound signal, a further ultrasound signal with a further frequency spectrum is emitted in the direction of the part area of the hollow structure, in particular, by the ultrasound probe or by a further ultrasound probe. The bandwidth of the further frequency spectrum in this case is greater than the bandwidth of the frequency spectrum. Further reflected components of the further ultrasound signals are detected, in particular, by the ultrasound probe or by the further ultrasound probe. Depending on the further detected components, it is checked, (e.g., automatically), in particular by the evaluation unit, whether the part area of the hollow structure is hiding a further hollow structure or a further part area of the hollow structure in the direction of propagation of the further ultrasound signal. The ultrasound signal is emitted depending on a result of the check.

The direction of propagation of the further ultrasound signal corresponds in particular in this case to a potential or intended direction of propagation of the ultrasound signal.

The lower axial resolution of the ultrasound signal means that a further part area of the hollow structure lying in the axial direction behind the part area of the hollow structure, or the further hollow structure cannot be recognized with the aid of the ultrasound signal if the distance between the part area and the further hollow structure or the part area and the further part area is correspondingly small. The hiding of the further part area or the further hollow structure may be understood in this sense.

The higher bandwidth of the further ultrasound signal enables the possibly hidden further hollow structure or the possibly hidden further part area to be identified by the signal. For example, the ultrasound signal may only be emitted if it is established with the aid of the check that no further hollow structure or no further part area of hollow structure is hidden by the part area, or the direction of emission or direction of propagation of the further ultrasound signal may be adapted until such time as such hiding is no longer produced.

Thus, in particular falsifications of the response curve by reflections of particles that are present in the hidden further hollow structure or the hidden further part area may be avoided.

In accordance with a further aspect, an ultrasound system for characterization of particles in a fluid-filled hollow structure is specified, which is configured to carry out the method described above. The ultrasound system has an ultrasound probe, (e.g., an endocorporeally insertable ultrasound probe), which is configured to emit in the direction of a part area of the hollow structure an ultrasound signal with a frequency spectrum that has a local maximum at a variable measurement frequency and to detect reflected components of the ultrasound signal. The ultrasound system has a control unit for actuating the ultrasound probe that is designed to tune the measurement frequency in a predetermined measurement interval, in particular to tune it automatically. The ultrasound system, (e.g., the control unit), has an evaluation unit that is configured, depending on the detected reflected components, to detect a spectral response curve as a function of the measurement frequency and depending on the response curve to determine at least one characteristic property for at least one part of the particles that is located in the part area of the hollow structure.

In particular, the ultrasound probe is configured, actuated by the control unit, to create the ultrasound signal with frequencies in the measurement interval.

The evaluation unit and the control unit may thus be combined in different forms of embodiment or be configured separately from one another.

In accordance with at least one form of embodiment of the ultrasound system, the ultrasound probe is configured to create the ultrasound signal, in particular actuated by the control unit, in such a way that the measurement interval lies within a range of 5 MHz to 12 MHz.

In accordance with at least one form of embodiment, the ultrasound probe is configured to create the ultrasound signal with a bandwidth of the frequency spectrum that is greater than or equal to 1 kHz and less than or equal to 100 kHz.

Further forms of embodiment follow directly from the various forms of embodiment of the method and vice versa. In particular, the ultrasound system may be configured to carry out a method as disclosed herein.

In accordance with a further aspect, a computer program with commands is specified. When the computer program or the commands are executed by an ultrasound system, in particular by the control unit and/or the evaluation unit of the ultrasound system, the commands cause the ultrasound system to carry out a method.

In accordance with a further aspect, a computer-readable memory medium is specified, which stores a computer program.

The computer program and also the computer-readable memory medium may be understood as respective computer program products with the commands.

Further features of the disclosure emerge from the claims, the figures, and the description of the figures. The features and combinations of features mentioned here in the description as well as the features and combinations of features mentioned below in the description of the figures and/or shown in the figures may not only be included in the combination specified in each case but also in other combinations in the disclosure. In particular, versions and combinations of features are also included in the disclosure that do not have all features of a claim as originally formulated. What is more, embodiments and feature combinations of the disclosure are included that go beyond the combinations of features set out in the references of the claims or which differ from these.

DETAILED DESCRIPTION

Figure 1:
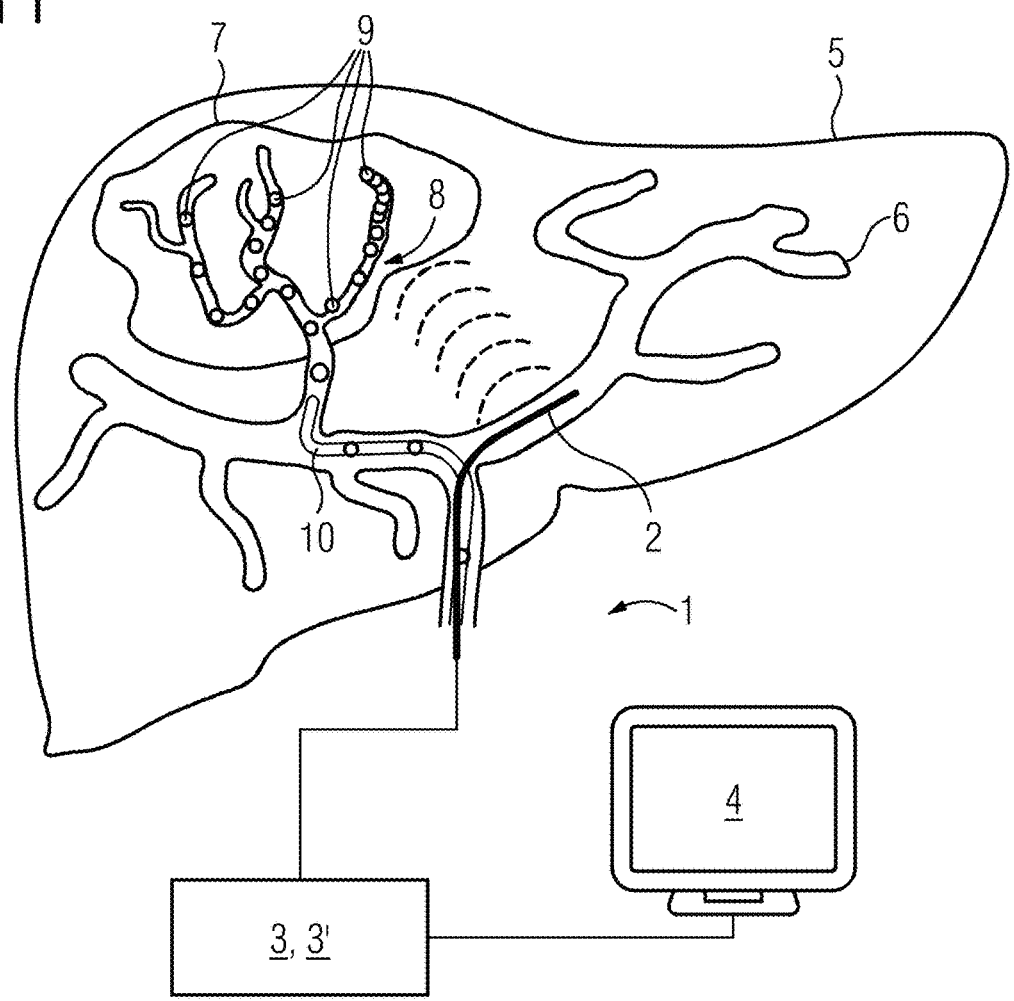
FIG. 1 depicts a schematic diagram of an example of a form of embodiment of an ultrasound system.

Shown in FIG. 1 is a schematic diagram of an example of a form of embodiment of an ultrasound system 1. The ultrasound system 1 has an ultrasound probe 2, a control unit 3, which for actuation of the ultrasound probe 2 is connected to the latter. The ultrasound system 1 also includes an evaluation unit 3', which is connected to the ultrasound probe 2 and/or the control unit 3. The control unit 3 and the evaluation unit 3', in various forms of embodiment, may be implemented in a common control and evaluation unit or as separate units.

The control unit 3 may actuate the ultrasound probe 2, so that the probe creates an ultrasound signal with an adjustable or variable measurement frequency. In this case, an ultrasound signal with a specific frequency may be understood as an ultrasound signal with a frequency spectrum that has a local maximum at the specific frequency, e.g., the measurement frequency here.

The ultrasound signal may be emitted in the direction of a fluid-filled hollow structure 8 of an object 5 and partly reflected, whereupon the reflected components may in their turn be detected by the ultrasound probe 2. The ultrasound probe 2 creates a corresponding measurement signal depending on the intensity of the reflected proportions and transfers the measurement signal to the evaluation unit 3'.

The object 5 may involve a part of the body or an organ of a human being. The fluid-filled hollow structure 8 may involve a blood vessel or a part of a vessel tree. In particular, the hollow structure 8 is located at least partly in a relevant region of interest 7, which may correspond to a tumor or the like. The control unit 3 is configured to tune the measurement frequency in a predetermined measurement interval and the evaluation unit 3' is designed accordingly to acquire a spectral response curve as a function of the respective reflected components of the ultrasound signal. The intensity of the reflected components, thus also the measurement signal and thus the spectral response curve, is influenced by at least one characteristic property of particles 9 that are located in the fluid-filled hollow structure 8. The particles 9 involve previously introduced embolization beads, which where necessary may also elute a medicament.

The shape and/or height of the spectral response curve may in particular depend on the local concentration of particles 9 and/or on their mobility. The mobility of the particles in this case may depend in particular on adhesion of the particles 9 to inner walls of the hollow structure 8, instruments or the like. On the other hand, location and amount of the adhering particles are of great interest for a person carrying out the treatment.

The greater the concentration of the particles 9 in the correspondingly analyzed part area of the hollow structure 8 is, the greater the intensity of the reflected components tends to be, in particular if a resonance condition in respect of the measurement frequency is present. The greater is the proportion of adhering particles 9 compared to the particles 9 able to move freely in the fluid, the more heavily distributed and/or shifted is the response curve compared to a reference curve, wherein the reference curve describes the theoretical or idealized frequency response of freely moving particles 9 in the fluid.

Figure 2:
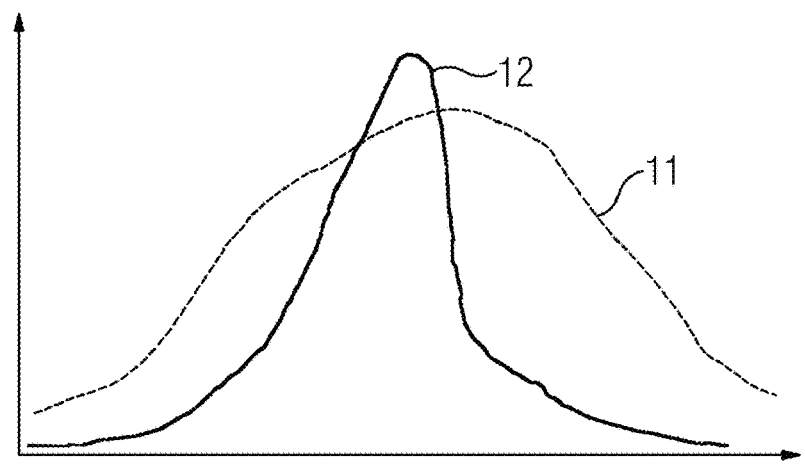
FIG. 2 depicts a schematic diagram of a response curve in accordance with an example of a form of embodiment of a method and also a reference curve.

This is shown schematically in FIG. 2. Shown in FIG. 2 as a dashed line are the response curve 11 as a function of the measurement frequency and the reference curve 12 as a solid line. The resonance peak of the response curve 11 is widened or shifted to higher frequencies here compared to the resonance peak of the reference curve 12 by the adhesion of a part of the particles 9 to the inner wall of the hollow structure.

From the widening and/or shifting of the resonance peak, the evaluation unit 3' may deduce the proportion of the adhering particles 9. From the amplitude of the response curve 11 at the resonant frequency or from the maximum amplitude of the response curve 11, the evaluation unit 3' may deduce the local concentration of the particles 9 in the correspondingly analyzed part area of the hollow structure 8.

The particles 9 may involve embolization beads, which are introduced by a catheter 10 beforehand into the vessel tree 6 and in this way are partly also forced forward into the hollow structure 8 or the analyzed part area of the hollow structure 8. The described evaluation of the response curve 11 by the evaluation unit 3' thus enables a user to check the current status of the embolization or the progress or the success or the embolization.

In various forms of embodiment, the ultrasound system 1 has a display 4, which is connected to the evaluation unit 3'.

The evaluation unit 3' may then actuate the display 4, in order to display on the latter, the at least one characteristic property of the particles 9 encoded in color and/or brightness, for example, as an overlay on a conventional B-mode scan, for example.

In various forms of embodiment, as outlined in FIG. 1, the ultrasound probe 2 may be embodied as an endovascular insertable ultrasound probe 2, in particular, at least partly able to be introduced into the vessel tree 6. In this way, higher frequencies are possible, because a shorter range is required. The higher frequencies in their turn lead to an improved spatial resolution. In other forms of embodiment, the ultrasound probe 2 may be embodied as a conventional ultrasound probe 2, which is applied from outside the body.

In accordance with various forms of embodiment, e.g., via the width and/or shape of the response curve 11 with the aid of the spectral ultrasound resonance of the particles 9, information about the spatial distribution of particles 9 swimming freely in the fluid or adhering is determined.

To do this, an ultrasound probe operating at high frequency may be inserted, for example, endovascularly. The measurement frequency of the ultrasound probe is tunable, so that at least two different frequency spectra with corresponding local maxima may be emitted and received. A corresponding narrow size dispersion of the particles 9 or of the embolization beads makes possible a good definition of the ultrasound resonance curve, e.g., of the response curve 11. Because the spectral resonance response of an individual particle 9 is dependent on whether the particle 9 is swimming freely in the fluid or whether it is adhering to something, the characteristic properties of the particles 9 on average may be analyzed by the response curve 11.

In various forms of embodiment, the ultrasound reflection, for example, in B-mode, is measured as a narrowband measurement with the ultrasound probe, in particular endovascularly. The measurement frequency is tuned and, for each relevant location in the tissue being examined or in the object being examined, a corresponding spectral response curve as described is recorded. The response curve may be recorded in this case at the basic frequency of the measurement frequency or at higher harmonics or in a combination. For each measured section of the hollow structure in the target region the spectral response curve is evaluated accordingly. The strength of the signal, in particular in the range of the resonant frequency, may correspond to the amount of particles of the concentration of particles in this region. A widening and/or shifting of the resonance peak corresponds to an adhesion of the particles in this region. The more the resonance peak is widened or shifted, the greater is the proportion of adhering particles. The proportion of adhering particles may be determined via a correlation, (e.g., a value of a convolution integral), between measured frequency response and the idealized frequency response of freely moving particles, (e.g., between the response curve and the reference curve). As an alternative or in addition, a curve fit may be carried out, with the aid of which width and central frequency of the resonance peak may be determined and reconciled.

The narrowband measurement leads to temporally longer pulses, so that the axial resolution of the ultrasound measurement falls correspondingly. Therefore it may be provided by a conventional wideband B-node ultrasound scan that two hollow structures filled with particles do not lie closely behind one another. If this is the case, the alignment of the ultrasound may be adapted accordingly. Optionally, an automatic algorithm may be employed, which checks this condition and enables the analysis with the aid of the narrowband ultrasound signal, provided no corresponding hollow structures lying behind one another are present in the target region.

Via the wideband B-mode scan, (e.g., the B-mode scan with temporally short pulses), a registration may also be determined, so that with the resonance signal determined in the narrowband measurement, (e.g., the response curve), the respective section may be assigned to the hollow structure and for example the measurement result may then be displayed for this section.

Between the individual B-mode images at various frequencies, an image-based movement correction may be undertaken. For this, in various forms of embodiment, for example, a narrowband ultrasound at the respective measurement frequency with long pulses for resonance measurement and a wideband ultrasound with short pulses for the imaging necessary for the movement correction may be employed alternately.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for characterization of a mobility of particles in a fluid-filled blood vessel, the method comprising:
    emitting an ultrasound signal with a frequency spectrum, which has a local maximum at a variable measurement frequency, in a direction of a part area of the fluid-filled blood vessel;
    detecting reflected components of the ultrasound signal as a result of an ultrasound reflection of the ultrasound signal;
    tuning the variable measurement frequency in a predetermined measurement interval;
    acquiring a spectral response curve of the ultrasound reflection as a function of the variable measurement frequency based on the reflected components; and
    determining a restriction of movement of the particles in a fluid of the fluid-filled blood vessel via: (1) an adhesion of the particles to an inner wall of the fluid-filled blood vessel, or (2) an adhesion of the particles to a medical instrument in the fluid-filled blood vessel, wherein the restriction of movement is deduced via at least one curve property of the spectral response curve of the ultrasound reflection,
    wherein the restriction of movement of the particles reflects a mobility of the particles located in the part area of the fluid-filled blood vessel, and
    wherein the particles are embolization beads having diameters in a range of 10 micrometers to 500 micrometers.

2. The method of claim 1, further comprising:
    determining an additional measure for an amount of the particles located in the part area of the fluid-filled blood vessel based on the spectral response curve of the ultrasound reflection.

3. The method of claim 2, further comprising:
    determining an amplitude value of the spectral response curve of the ultrasound reflection at a predefined frequency value of the variable measurement frequency in the predetermined measurement interval,
    wherein the additional measure is determined depending on the amplitude value.

4. The method of claim 3, wherein the predefined frequency value corresponds to a local maximum point of the spectral response curve of the ultrasound reflection.

5. The method of claim 1, further comprising:
    comparing the at least one curve property of the spectral response curve of the ultrasound reflection with at least one predetermined reference curve property,
    wherein the restriction of movement of the particles is determined based on a result of the comparing.

6. The method of claim 5, wherein the at least one curve property of the spectral response curve of the ultrasound reflection comprises a widening and a shifting of a resonance peak of the spectral response curve of the ultrasound reflection, and
    wherein the widening and/or the shifting, with respect to the at least one predetermined reference curve property, of the resonance peak of the spectral response curve of the ultrasound reflection corresponds to the restriction of movement of the particles.

7. The method of claim 6, wherein a strength of the spectral response curve of the ultrasound reflection corresponds to an amount of the particles located in the part area of the fluid-filled blood vessel.

8. The method of claim 1, further comprising:
    determining a characteristic correlation value based on the spectral response curve of the ultrasound reflection and a reference curve,
    wherein the restriction of movement is determined based on the characteristic correlation value.

9. The method of claim 1, wherein the predetermined measurement interval lies within a range of 5 MHz to 12 MHz.

10. The method of claim 1, wherein a bandwidth of the frequency spectrum of the emitted ultrasound signal is greater than or equal to 1 kHz and less than or equal to 100 kHz.

11. The method of claim 1, further comprising:
    emitting a further ultrasound signal with a further frequency spectrum in the direction of the part area of the fluid-filled blood vessel before the emitting of the ultrasound signal, wherein a bandwidth of the further frequency spectrum is greater than a bandwidth of the frequency spectrum;
    detecting further reflected components of the further ultrasound signal; and
    checking, based on the further reflected components, whether the part area of the fluid-filled blood vessel is hiding a further blood vessel or a further part area of the fluid-filled blood vessel in a direction of propagation of the further ultrasound signal,
    wherein the ultrasound signal is emitted based on a result of the check.

12. The method of claim 1, wherein the medical instrument is a catheter or a guide wire.

13. The method of claim 1, wherein the determining of the restriction of movement is via both the adhesion of the particles to the inner wall of the fluid-filled blood vessel and the adhesion of the particles to the medical instrument in the fluid-filled blood vessel.

14. An ultrasound system for characterization of a mobility of particles in a fluid-filled blood vessel, the ultrasound system comprising:
   an ultrasound probe configured to emit an ultrasound signal with a frequency spectrum that has a local maximum at a variable measurement frequency, in a direction of a part area of the fluid-filled blood vessel and to detect reflected components of the ultrasound signal as a result of an ultrasound reflection of the ultrasound signal;
   a control unit configured to actuate the ultrasound probe, which is configured to tune the variable measurement frequency in a predetermined measurement interval; and
   an evaluation unit configured to acquire a spectral response curve of the ultrasound reflection as a function of the variable measurement frequency based on the reflected components, and determine a restriction of movement of the particles in a fluid of the fluid-filled blood vessel via: (1) an adhesion of the particles to an inner wall of the fluid-filled blood vessel, or (2) an adhesion of the particles to a medical instrument in the fluid-filled blood vessel, wherein the restriction of movement is deduced via at least one curve property of the spectral response curve of the ultrasound reflection,
   wherein the restriction of movement of the particles reflects a mobility of the particles located in the part area of the fluid-filled blood vessel, and
   wherein the particles are embolization beads having diameters in a range of 10 micrometers to 500 micrometers.

15. The ultrasound system of claim 14, wherein the ultrasound probe is an endocorporeally insertable ultrasound probe.

16. The ultrasound system of claim 14, wherein the at least one curve property of the spectral response curve of the ultrasound reflection comprises a widening and a shifting of a resonance peak of the spectral response curve of the ultrasound reflection, and
   wherein the widening and/or the shifting, with respect to at least one predetermined reference curve property, of the resonance peak of the spectral response curve of the ultrasound reflection corresponds to the restriction of movement of the particles.

17. The ultrasound system of claim 16, wherein a strength of the spectral response curve of the ultrasound reflection corresponds to an amount of the particles located in the part area of the fluid-filled blood vessel.

18. The ultrasound system of claim 14, wherein the ultrasound probe is configured to create the ultrasound signal so that the predetermined measurement interval lies within a range of 5 MHz to 12 MHz.

19. The ultrasound system of claim 14, wherein the ultrasound probe is configured to create the ultrasound signal with a bandwidth of the frequency spectrum that is greater than or equal to 1 kHz and less than or equal to 100 kHz.

20. A non-transitory computer program product with commands that, when executed by an ultrasound system, cause the ultrasound system to:
   emit, by an ultrasound probe of the ultrasound system, an ultrasound signal with a frequency spectrum, which has a local maximum at a variable measurement frequency, in a direction of a part area of a fluid-filled blood vessel;
   detect, by the ultrasound probe, reflected components of the ultrasound signal as a result of an ultrasound reflection of the ultrasound signal;
   actuate the ultrasound probe by a control unit of the ultrasound system;
   tune, by the control unit, the variable measurement frequency in a predetermined measurement interval;
   acquire, by an evaluation unit of the ultrasound system, a spectral response curve of the ultrasound reflection as a function of the variable measurement frequency based on the reflected components; and
   determine, by the evaluation unit, a restriction of movement of particles in a fluid of the fluid-filled blood vessel via: (1) an adhesion of the particles to an inner wall of the fluid-filled blood vessel, or (2) an adhesion of the particles to a medical instrument in the fluid-filled blood vessel, wherein the restriction of movement is deduced via at least one curve property of the spectral response curve of the ultrasound reflection,
   wherein the restriction of movement of the particles reflects a mobility of the particles located in the part area of the fluid-filled blood vessel, and
   wherein the particles are embolization beads having diameters in a range of 10 micrometers to 500 micrometers.

21. The non-transitory computer program product of claim 20, wherein the at least one curve property of the spectral response curve of the ultrasound reflection comprises a widening and a shifting of a resonance peak of the spectral response curve of the ultrasound reflection, and
   wherein the widening and/or the shifting, with respect to at least one predetermined reference curve property, of the resonance peak of the spectral response curve of the ultrasound reflection corresponds to the restriction of movement of the particles.

22. The non-transitory computer program product of claim 21, wherein a strength of the spectral response curve of the ultrasound reflection corresponds to an amount of the particles located in the part area of the fluid-filled blood vessel.

* * * * *